US00RE45164E

(19) United States
(12) Reissued Patent
Chen et al.

(10) Patent Number: US RE45,164 E
(45) Date of Reissued Patent: Sep. 30, 2014

(54) CABLE CLIP

(71) Applicants: Hsuan-Yu Chen, Taipei Hsien (TW); Tien-Wen Lin, Taipei Hsien (TW); Po-Hsuan Yu, Taipei Hsien (TW); Jia-Jiann Huang, Taipei Hsien (TW)

(72) Inventors: Hsuan-Yu Chen, Taipei Hsien (TW); Tien-Wen Lin, Taipei Hsien (TW); Po-Hsuan Yu, Taipei Hsien (TW); Jia-Jiann Huang, Taipei Hsien (TW)

(73) Assignee: Acbel Polytech Inc., Tamshui Chen, Taipei Hsien (TW)

(21) Appl. No.: 13/840,636

(22) Filed: Jun. 13, 2013

Related U.S. Patent Documents

Reissue of:
(64) Patent No.: 7,837,158
Issued: Nov. 23, 2010
Appl. No.: 12/460,958
Filed: Jul. 27, 2009

(30) Foreign Application Priority Data

Apr. 30, 2009 (TW) ..... 98114315 A

(51) Int. Cl.
*F16L 3/00* (2006.01)

(52) U.S. Cl.
USPC ..... 248/73

(58) Field of Classification Search
USPC ..... 248/65, 53, 67.5, 70, 73, 74.1
See application file for complete search history.

(56) References Cited

U.S. PATENT DOCUMENTS

| | | | | |
|---|---|---|---|---|
| 2,915,267 | A * | 12/1959 | Kaysing | 248/67.5 |
| 6,196,509 | B1 * | 3/2001 | Clemens | 248/302 |
| 2002/0187667 | A1 * | 12/2002 | Kitagawa et al. | 439/131 |

* cited by examiner

*Primary Examiner* — Anita M King
(74) *Attorney, Agent, or Firm* — C. G. Mersereau; Nikolai & Mersereau, P.A.

(57) ABSTRACT

A cable clip has a body and a fastener. The body has two supporting arms and a connecting arm. Each supporting arm has two ends. The connecting arm is formed between corresponding ends of the supporting arms. The fastener is mounted pivotally on the connecting arm of the body and has a through hole and multiple side surfaces. Distances from the through hole to the side surfaces of the fastener are different. Then, rotating the fastener adjusts the side surfaces abutting a plug to different plugs in different sizes.

20 Claims, 7 Drawing Sheets

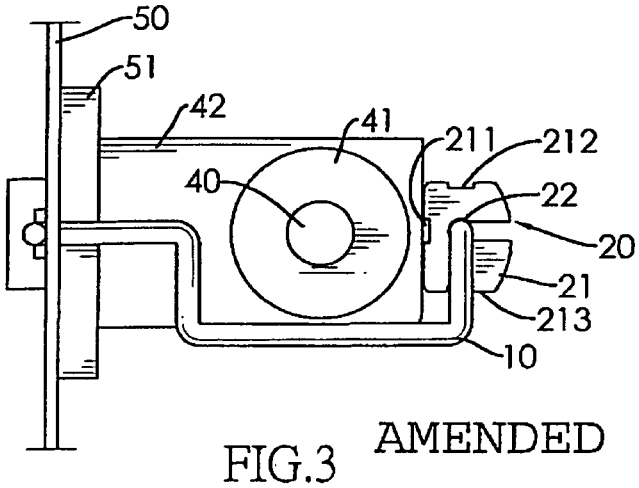
FIG.3 AMENDED
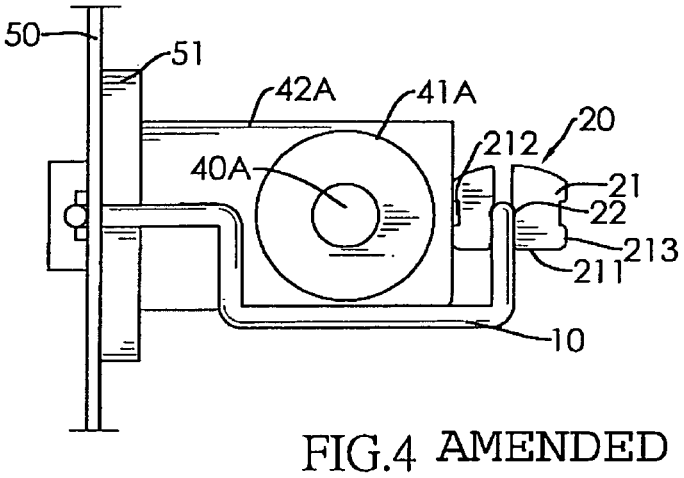
FIG.4 AMENDED
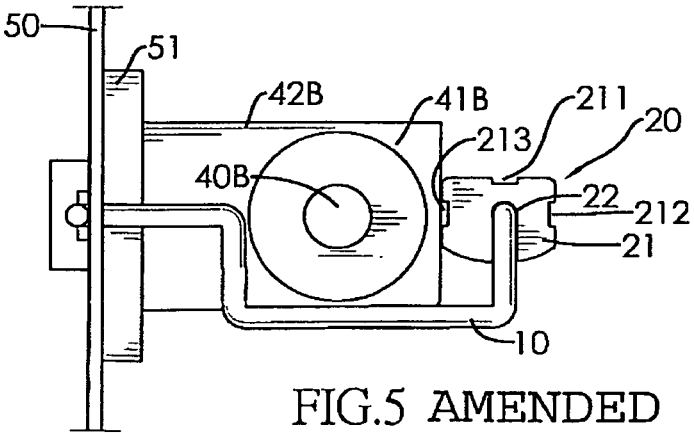
FIG.5 AMENDED

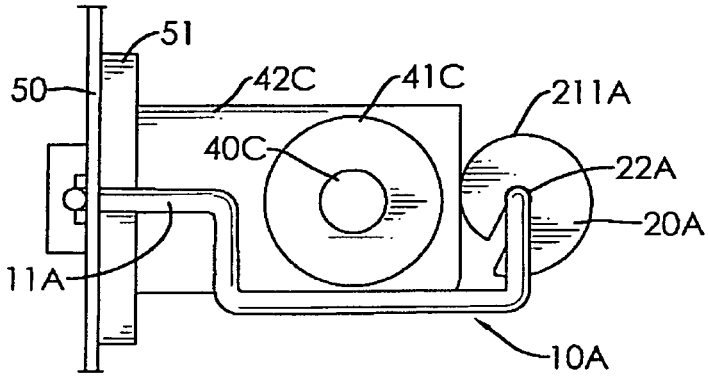
FIG.7 AMENDED
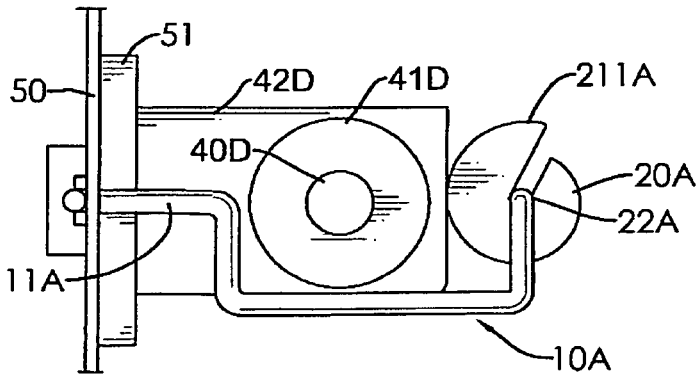
FIG.8 AMENDED

CABLE CLIP

Matter enclosed in heavy brackets [ ] appears in the original patent but forms no part of this reissue specification; matter printed in italics indicates the additions made by reissue.

BACKGROUND OF THE INVENTION

1. Field of the Invention

The present invention relates to a clip, and more particularly to a cable clip that can fasten different plugs in different sizes.

2. Description of the Prior Arts

A cable clip is applicable for computer apparatus to fasten a plug of a power cable. With reference to FIG. 10, a conventional cable clip has two supporting arms (31) and a connecting arm (32). Each supporting arm (31) has two ends and a length. One supporting arm (31) is bent to define a recess (311). The recess (311) corresponds to a shape of a junction (41) of a power cable (40). The connecting arm (32) is formed between corresponding ends of the supporting arms (31). The other ends respectively of the supporting arms (31) are respectively mounted on a computer case (50) where installs a socket (51). When a plug (42) is inserted in the socket (51), the recess (311) engages the junction (41) of the power cable (40). Therefore, the plug (42) of the power cable (40) is fastened and avoid falling off.

The length of the supporting arms (31) of a conventional cable clip is fixed so one conventional cable clip only fastens the plug (42) with only one certain size. However, different plugs (42) have different sizes. When a user changes the plug (42), the original cable clip is useless and the user must change a new one. Changing a new cable clip is inconvenient and cost money.

To overcome the shortcomings, the present invention provides a cable clip to mitigate or obviate the aforementioned problems.

SUMMARY OF THE INVENTION

To main object of the invention is to provide a cable clip that can securely fasten a plug in different size.

A cable clip comprises a body and a fastener. The body has two supporting arms and a connecting arm. Each supporting arm has two ends. The connecting arm is formed between corresponding ends of the supporting arms. The fastener is mounted pivotally on the connecting arm of the body and has a through hole and multiple side surfaces. Distances from the through hole to the side surfaces of the fastener are different. Then, rotating the fastener adjusts the side surfaces abutting different plugs in different sizes.

Other objectives, advantages and novel features of the invention will become more apparent from the following detailed description when taken in conjunction with the accompanying drawings.

BRIEF DESCRIPTION OF THE DRAWINGS

FIGS. 3 to 5 are operational side views of the cable clip in FIG. 1, showing the fastener mounted in different directions;

FIGS. 7 and 8 are operational side views of the cable clip in FIG. 6, showing the fastener mounted in different directions;

DETAILED DESCRIPTION OF THE PREFERRED EMBODIMENTS

Figure 1:
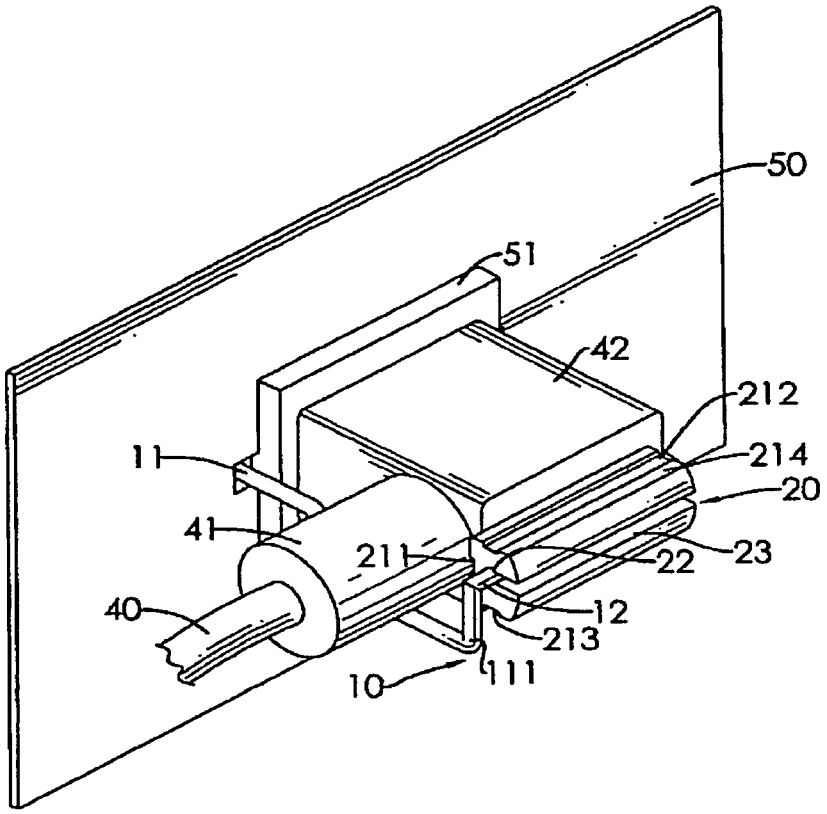
FIG. 1 is an operational perspective view of a first embodiment of a cable clip in accordance with the present invention, showing clamping a plug.
Figure 2:
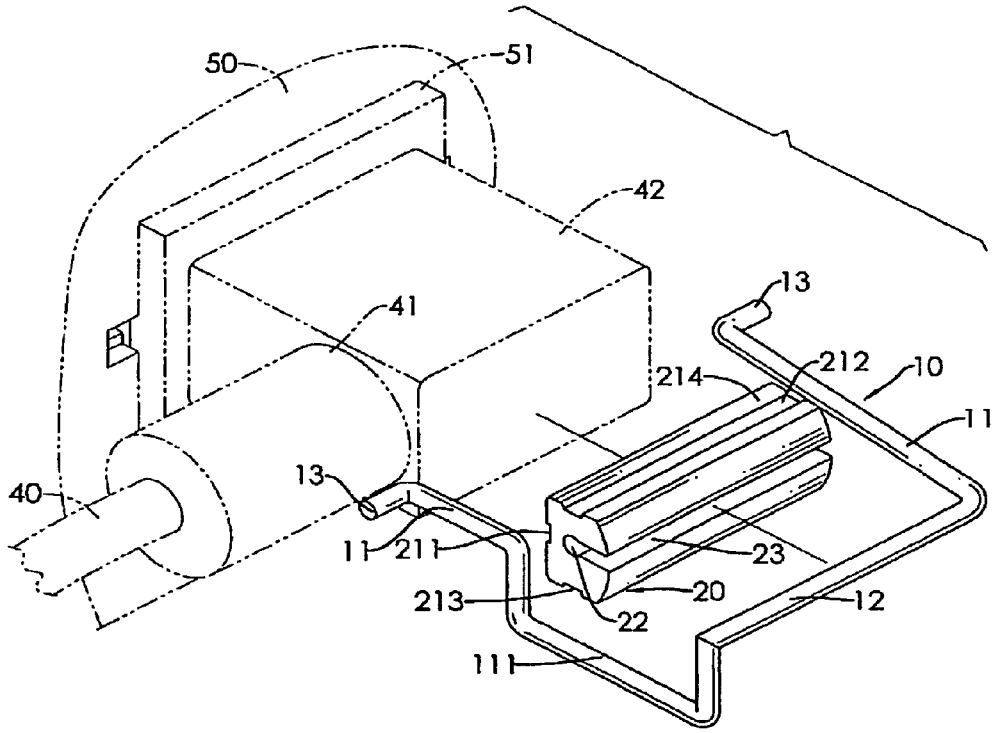
FIG. 2 is an exploded perspective view of the cable clip in FIG. 1 with a cable.

With reference to FIGS. 1 and 2, a cable clip in accordance with the present invention comprises a body (10) and a fastener (20).

The body (10) has two supporting arms (11), a connecting arm (12) and two positioning parts (13). Each supporting arm (11) has a positioning end and a connecting end. One supporting arm (11) is bent to define a recess (111). The recess (111) corresponds to the shape of a junction (41) of a power cable (40). The connecting arm (12) is formed between the connecting ends of the supporting arms (11). The positioning parts (13) respectively protrude from the positioning ends of the supporting arms (11) and are mounted on a computer case (50).

The fastener (20) is made by resilient material (e.g. plastic) and is mounted pivotally around the connecting arm (12) of the body (10) and has a through hole (22) and multiple side surfaces. The through hole (22) is formed through the fastener (20) and corresponds to and is mounted pivotally around the connecting arm (12) of the body (10). Distances from the through hole (22) to the side surfaces of the fastener (20) are different. Besides, the fastener (20) may have a gap (23). The gap (23) is formed through one side surface of the fastener (20) and communicates with the through hole (22) of the fastener (20) to allow the connecting arm (13) of the body (10) easily mounted through.

In a preferred embodiment, the fastener (20) is rectangular in cross section and has a first side surface (211), a second side surface (212), a third side surface (213) and multiple protrusions (214). The protrusions (214) protrude from the side surfaces (211, 212, 213) and abuts a plug (42) to increase friction. The first distance is defined between the through hole (22) and the first side surface (211). The second distance is defined between the through hole (22) and the second side surface (212). The third distance is defined between the through hole (22) and the third side surface (213). The second distance is longer than the first distance, and the third distance is longer than the second distance.

The plug (42) is installed on a computer case (50) and placed within the supporting arms (11) and the connecting arm (12). Rotating the fastener (20) adjusts the side surfaces (211, 212, 213) abutting the plug (42) to adapt for plugs with different sizes. Besides, the recess (111) of the body (10) engages the junction (41) of the power cable (40) to fasten the plug (42) more stably.

With reference to FIGS. 3 to 5, the cable clip in accordance with the present invention is adapted for L-shape power cables (40, 40A, 40B). The L-shape power cables (40, 40A, 40B) have the junctions (41, 41A, 41B) and the plugs (42, 42A, 42B) being perpendicular to each other. The plugs (42, 42A, 42B) have different sizes With reference to FIG. 3, when the longest plug (42) is used, the first side surface (211) is adjusted to abut the longest plug (42). With reference to FIG. 4, when the medium plug (42A) is used, the second side surface (212) is adjusted to abut the medium plug (42A). With reference to FIG. 5, when the shortest plug (42B) is used, the third side surface (213) is adjust to abut the plug (42B).

Figure 6:
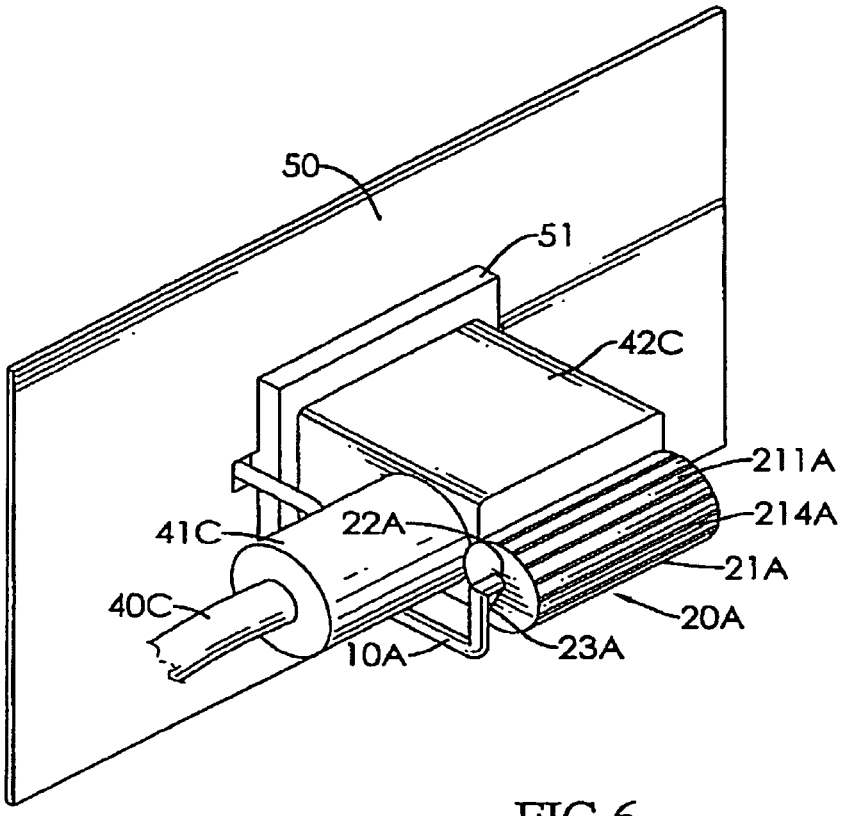
FIG. 6 is a perspective view of a second embodiment of the cable clip in accordance with the present invention.

With reference to FIG. 6, in another preferred embodiment, the fastener (20A) is a column (21A) and has annular side surfaces (211A). The through hole (22A) is formed eccentrically through the fastener (20A). The thickness of the fastener (20A) from the through hole (22A) to annular side surfaces (211A) in different directions are different, so rotating the fastener (20A) adjusts different part abutting the plug (42C) to adapt for different plugs in different sizes. Besides, the annular side surfaces (211A) may have an embossed surface (214A) to increase friction when abutting the plug (42C).

With reference to FIGS. 7 and 8, the cable clip in accordance with the present invention clamps the plugs (42C, 42D) with two different sizes. Comparing to aforementioned embodiment that the fastener (20) abuts the plug (40, 40A, 40B) by the face, the fastener (20A) abuts the plug (40C, 40D) by a line. The line and the supporting arms (11A) align with each other to offer stable fixed-effects.

With reference to FIG. 7, when the longer plug (42C) is used, the annular side surfaces (211A) with smaller thickness are adjusted to abut the plug (42C). With reference to FIG. 8, when the shorter plug (42D) is used, the annular side surfaces (211A) with larger thickness are adjusted to abut the plug (42D).

Figure 9:
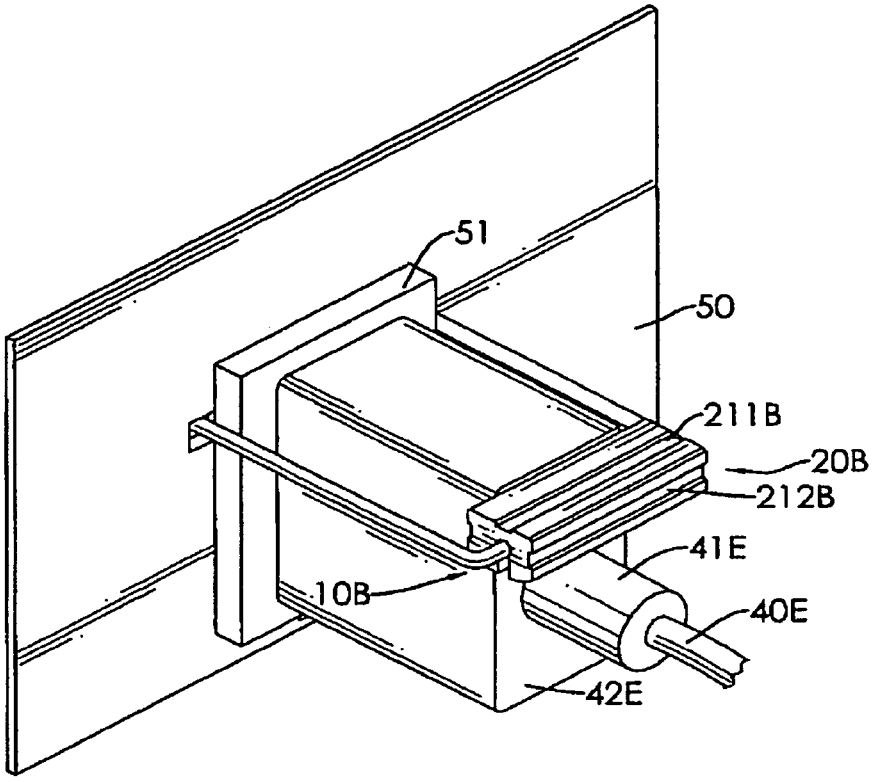
FIG. 9 is a perspective view of a third embodiment of a cable clip in accordance with the present invention.
Figure 10:
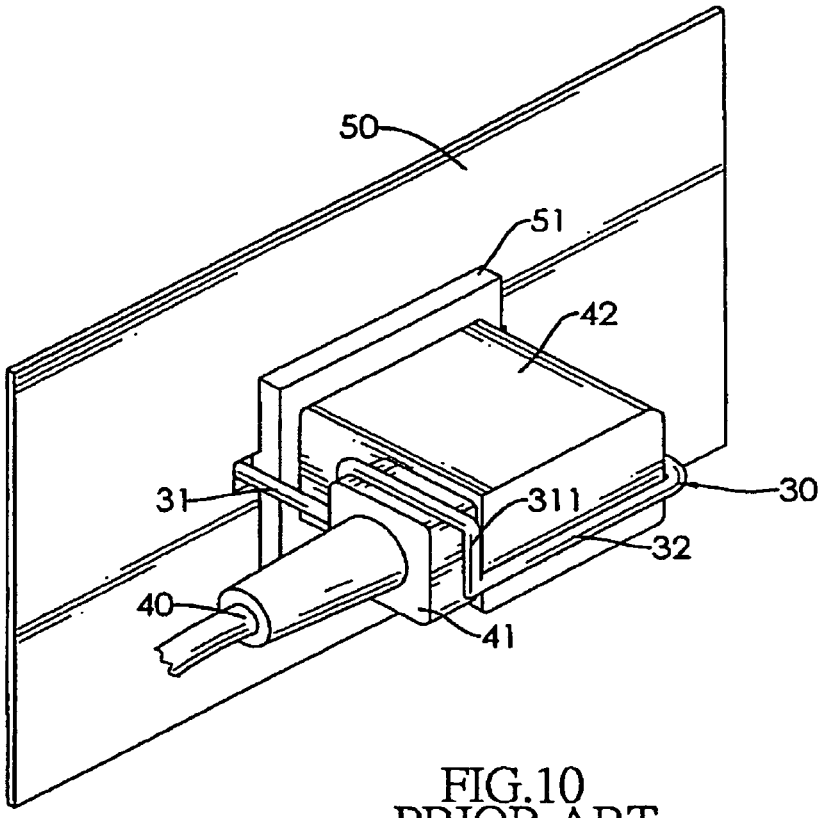
FIG.10 PRIOR ART
FIG. 10 is a perspective view of a conventional cable clip in accordance with the prior art.

With reference to FIG. 9, in still another preferred embodiment, the body (10B) is U-shape being adapted for linear type power cables (40E). The linear type power cable (40E) has the junction (41E) and the plug (42E) aligning with each other. Rotating the fastener (20B) adjusts side surface (211B, 212B, 213B) abutting the plug (42E) to adapt for plugs with different sizes and can offer the plug (42E) to installed stably in the socket (51).

Therefore, the cable clip in accordance with the present invention fastens securely plugs by the body (10) and the fastener (20). When the cable clip as described is used for fastening a plug, rotating the fastener (20) to adjust the side surfaces of the fastener (20) abutting the plug (42) is flexibly and easily.

Even though numerous characteristics and advantages of the present invention have been set forth in the foregoing description, together with details of the structure and features of the invention, the disclosure is illustrative only. Changes may be made in the details, especially in matters of shape, size, and arrangement of parts within the principles of the invention to the full extent indicated by the broad general meaning of the terms in which the appended claims are expressed.

What is claimed is:

1. A cable clip comprising:

a body having two supporting arms and each supporting arm having a positioning end and a connecting end;

a connecting arm formed between the connecting ends of the supporting arms; and two positioning parts respectively protruding from the positioning ends respectively of the supporting arms; and a fastener mounted pivotally around the body and having a through hole formed through the fastener and corresponding to and mounted pivotally around the connecting arm of the body; and multiple side surfaces, wherein distances from the through hole to the side surfaces are different.

2. The cable clip as claimed in claim 1, wherein the fastener is rectangular in cross section and has a first side surface, a second side surface and a third side surface.

3. The cable clip as claimed in claim 2, wherein the fastener further has a gap formed through one side surface of the fastener and communicates with the through hole of the fastener.

4. The cable clip as claimed in claim 3, wherein one supporting arm of the body is bent to define a recess.

5. The cable clip as claimed in claim 2, wherein one supporting arm of the body is bent to define a recess.

6. The cable clip as claimed in claim 2, wherein the fastener further has multiple protrusions protruding from the side surfaces.

7. The cable clip as claimed in claim 6, wherein the fastener further has a gap formed through one side surface of the fastener and communicates with the through hole of the fastener.

8. The cable clip as claimed in claim 7, wherein one supporting arm of the body is bent to define a recess.

9. The cable clip as claimed in claim 6, wherein one supporting arm of the body is bent to define a recess.

10. The cable clip as claimed in claim 1, wherein the fastener is a column and has annular side surfaces; and the through hole of the fastener is formed eccentrically through the fastener.

11. The cable clip as claimed in claim 10, wherein the side annular surfaces of the fastener have an embossed surface.

12. The cable clip as claimed in claim 11, wherein the fastener further has a gap formed through one side surface of the fastener and communicates with the through hole of the fastener.

13. The cable clip as claimed in claim 11, wherein one supporting arm of the body is bent to define a recess.

14. The cable clip as claimed in claim 10, wherein the fastener further has a gap formed through one side surface of the fastener and communicates with the through hole of the fastener.

15. The cable clip as claimed in claim 14, wherein one supporting arm of the body is bent to define a recess.

16. The cable clip as claimed in claim 10, wherein one supporting arm of the body is bent to define a recess.

17. The cable clip as claimed in claim 1, wherein the fastener further has a gap formed through one side surface of the fastener and communicates with the through hole of the fastener.

18. The cable clip as claimed in claim 17, wherein one supporting arm of the body is bent to define g a recess.

19. The cable clip as claimed in claim 1, wherein one supporting arm of the body is bent to define a recess.

20. The cable clip as claimed in claim 1, wherein the body is U-shape.

* * * * *